(12) United States Patent
Stark et al.

(10) Patent No.: US 8,596,109 B2
(45) Date of Patent: Dec. 3, 2013

(54) DEVICE FOR MEASURING THE CONCENTRATION OF PARAMAGNETIC GASES

(75) Inventors: Hartmut Stark, Stockelsdorf (DE); Peter Dreyer, Pansdorf (DE); Alfred Kelm, Badendorf (DE); Ralf Döring, Luebeck (DE); Anja Künzel, legal representative, Luebeck (DE); Günter Steinert, Bad Oldesloe (DZ)

(73) Assignee: Dräger Medical GmbH, Lübeck (DE)

( * ) Notice: Subject to any disclaimer, the term of this patent is extended or adjusted under 35 U.S.C. 154(b) by 230 days.

(21) Appl. No.: 13/020,403

(22) Filed: Feb. 3, 2011

(65) Prior Publication Data
US 2011/0252868 A1 Oct. 20, 2011

(30) Foreign Application Priority Data
Apr. 14, 2010 (DE) .................. 10 2010 014 883

(51) Int. Cl.
*G01N 27/74* (2006.01)

(52) U.S. Cl.
USPC ........................................ 73/25.02; 324/204

(58) Field of Classification Search
USPC .................. 73/25.01, 25.02, 25.03; 324/204
See application file for complete search history.

(56) References Cited

U.S. PATENT DOCUMENTS

| | | | | |
|---|---|---|---|---|
| 3,584,499 A * | 6/1971 | Hummel | .............. | 73/25.02 |
| 3,646,803 A * | 3/1972 | Meyer | .............. | 73/25.02 |
| 4,173,975 A * | 11/1979 | DeLong et al. | .............. | 128/204.22 |
| 4,667,157 A * | 5/1987 | Ciammaichella et al. | .... | 324/204 |
| 4,683,426 A * | 7/1987 | Hummel | .............. | 324/204 |
| 4,808,921 A * | 2/1989 | Christensen | .............. | 324/204 |
| 6,405,578 B2 * | 6/2002 | Chiba et al. | .............. | 73/25.02 |
| 6,430,987 B1 | 8/2002 | Stark | | |
| 7,752,886 B2 * | 7/2010 | Haveri et al. | .............. | 73/24.01 |
| 2001/0045121 A1* | 11/2001 | Chiba et al. | .............. | 73/25.02 |
| 2004/0045340 A1* | 3/2004 | Steinert et al. | .............. | 73/25.02 |
| 2004/0083789 A1 | 5/2004 | Stark et al. | | |
| 2007/0227230 A1* | 10/2007 | Haveri et al. | .............. | 73/24.01 |
| 2011/0094293 A1* | 4/2011 | Klein | .............. | 73/31.05 |

FOREIGN PATENT DOCUMENTS

| | | |
|---|---|---|
| DE | EP 0 285 833 A2 | 10/1988 |
| DE | 100 37 380 Al | 5/2001 |
| DE | 102 41 244 Cl | 8/2003 |
| DE | 102 51 130 Al | 5/2004 |
| DE | 202004015400 U1 | 12/2004 |

* cited by examiner

*Primary Examiner* — Lisa Caputo
*Assistant Examiner* — Punam Roy
(74) *Attorney, Agent, or Firm* — McGlew and Tuttle, P.C.

(57) ABSTRACT

A device for measuring the concentrations of paramagnetic gases in a gas sample has at least one modulatable magnetic flux source, which has an air gap, to which a gas sample can be fed. A controllable power source, for generating current and voltage signals, is coupled with the modulatable magnetic flux source in order to generate a modulatable magnetic flux within the air gap. Two measuring points are arranged at least partly within the air gap. Each measuring point has an electrically controllable heating device and a heat conduction-measuring unit or resistive measuring device. Each measuring point is coupled with a variable power source to heat the heating device to a working temperature. Each measuring point is coupled with a measuring circuit to measure heat conduction measured signals generated by the heat conduction-measuring unit, from which the concentrations of paramagnetic gases, which are contained in the gas sample, can be derived.

19 Claims, 11 Drawing Sheets

DEVICE FOR MEASURING THE CONCENTRATION OF PARAMAGNETIC GASES

CROSS REFERENCE TO RELATED APPLICATIONS

This application claims the benefit of priority under 35 U.S.C. §119 of German Patent Application DE 10 2010 014 883.0 filed Apr. 14, 2010 the entire contents of which are incorporated herein by reference.

FIELD OF THE INVENTION

The present invention pertains, in general, to a device for measuring the physical properties of gases. The present invention pertains, in particular, to a device for measuring the concentrations of paramagnetic gases in a gas sample, for example, the concentrations of oxygen and other added gases in the breathing gas of a patient to be respirated and/or anesthetized.

BACKGROUND OF THE INVENTION

Paramagnetic methods, which are based on the fact that oxygen molecules are paramagnetic based on their permanent magnetic dipole moment, whereas most other gases are diamagnetic, are frequently used to determine the oxygen concentration in gases. It is generally known that the heat conductivity changes in paramagnetic gases (for example, $O_2$ and NO) under the effect of magnetic fields. The cause of this behavior is obviously the fact that paramagnetic gases have a permanent magnetic moment, but this is not normally manifested towards the outside because of the thermal motion of the molecules. However, a sufficiently strong external magnetic field ensures that the magnetic dipole moments of the individual molecules are aligned. This brings about, on the one hand, a change in susceptibility, which leads to an increase in magnetic flux, and, on the other hand, a certain molecular arrangement becomes established in the gas, as a result of which the possibility of transmitting heat energy to adjacent molecules by shocks is limited. Consequently, the heat conductivity of the gas changes to a small extent.

In a prior-art measuring device, which is based on this phenomenon, the gas sample to be analyzed is located in a cylindrical vessel, in the longitudinal axis of which a thin measuring wire heated to a working temperature is arranged. If the heat conductivity of the gas changes due to an external magnetic field, this brings about a change in the resistance of the measuring wire, which change can be determined with a measuring bridge.

Complex fresh gas mixtures, which contain in most cases a binary basic mixture of oxygen and nitrogen, laughing gas or xenon and one of the common inhalation anesthetics (for example, desflurane, sevoflurane, isoflurane, enflurane, and halothane), are at times used in anesthesia for respirating patients in medical technology. It is frequently necessary for monitoring the patient to also carry out a determination of the gas concentrations during the expiration phase of the patient. The gas mixture additionally contains carbon dioxide, water vapor and possibly other metabolites, for example, ethyl alcohol, methane and acetone, besides said gases, during the expiration phase. Concerning the relevant gas concentrations, interest is limited here mainly to oxygen, carbon dioxide and the anesthetic as well as the dynamic changes of these components over time. Therefore, there is a need for cost-effective measuring devices, which detect such gases at the required resolution and possibly free from cross sensitivities. Several independent sensors, which are optimized for the particular target gas, are usually used for this.

It is known, for instance, the use of multichannel infrared optical analyzers with heat radiation sources, which are used to measure infrared-active gases and are capable of analyzing a gas mixture at a plurality of wavelengths for their absorption properties. Based on the spectra, which are recorded at least partly, the individual gaseous components can then be determined in terms of their concentration if they have sufficient and specific IR absorptions. However, gases such as oxygen, nitrogen, helium and xenon cannot be detected with this method.

Furthermore, sensors based on infrared laser diodes, which are capable, based on the narrow-band emission characteristic, to resolve the likewise narrow absorption lines of oxygen are known. However, a minimum absorption length, which leads to an unfavorable size of the sensor, is necessary because of the small absorption cross sections to carry out a concentration measurement with sufficient accuracy with this method. Moreover, interactions occur between the gases involved, which may at times require a correction of the measured $O_2$ concentration values. Furthermore, this method is not suitable for the direct determination of the other gas components. Finally, this method, like the above-mentioned methods as well, is relatively expensive because of the high-quality optical components, especially because the laser diodes used have aging effects, which limit their service life.

Even though electrochemical sensors represent a cost-effective alternative to the IR optical methods, they meaningfully permit only a measurement of the oxygen concentration and—with great restrictions—of the carbon dioxide concentration. Anesthetic gases and noble gases cannot be measured in this manner.

In fixed electrolyte sensors, for example, those known from DE 20 2004 015 400 U1, a solid, for example, zirconium dioxide, assumes the task of an ion conductor. Thus, even though such sensors do have primarily a good selectivity for oxygen, they bring about decomposition processes in medical gas mixtures under certain circumstances because of the high operating temperature that is necessary to make ion conduction possible. The halogenated hydrocarbons commonly used in anesthesia are, in particular, no longer stable at operating temperatures of about 600° C. and at times produce highly toxic reaction products. In addition, laughing gas, which is also used in anesthesia, tends to decompose into nitrogen and oxygen at temperatures beginning from 400° C. and toxic nitrogen oxides may be formed as well. The oxygen released in this process will then lead to a falsely elevated concentration display. Oxygen concentrations can be reasonably measured with this principle of measurement in nitrogen/oxygen mixtures only. Other gases do not lend themselves to the analysis. However, this method is capable of detecting the flow parameter, which is likewise important, if the sensor is used in the mainstream.

Gas sensors based on heat conductivity are known from the literature, which operate either with heated metal wires or with resistive heating structures, which are applied to the membranes of microstructured silicon elements. The fact that the excess temperature of the wire or of the microstructured heating structure becomes established at a given electric heating energy as a function of the heat conduction properties of the carrier structure and of the gases surrounding the heating means is utilized in these sensors. The concentration ratios of binary gas mixtures can be unambiguously determined with such structures if the components of these mixtures have sufficiently different specific heat conductivities. Gas mixtures containing more than two components cannot be measured with this method. In particular, nitrogen/oxygen mixtures with additions of, for example, water vapor or $CO_2$ cannot be meaningfully analyzed with this because of the similar specific heat conductivities of $O_2$ and $N_2$.

A gas sensor based on heat conduction, which utilizes the fact that the heat conductivity values of gases have certain temperature dependences, whose extent depends on the molecular structure of the gas in question, is known from EP 0 285 833 A2. It is proposed in that document that the gas sample to be analyzed at different measuring temperatures one after another and the concentrations of the different gases be inferred from the heat conductivity values measured at different temperatures. Mixtures containing three or more components can thus be analyzed, in principle. However, the requirement for this is a linear independence of the measured data sets, which is guaranteed in the normal case to a limited extent only. In addition, the sequential measurement in time presupposes a stable composition of the gas mixture at least for the duration of the analysis. The additional pneumatic means necessary for this make such a sensor expensive and adversely affect the overall size. Selective measurement of the oxygen concentration is not possible in this manner.

Documents DE 100 37 380 A1, DE 102 51 130 A1 and DE 102 41 244 C1 describe means that utilize the magnetic field-dependent heat conductivity of the oxygen component in gas mixtures for the concentration determination. The magnetic flux density is cyclically varied in these means in the measuring gap of an electromagnet and the heat conductivity of the gas mixture, which varies in the process, is detected with a heat conductivity measuring chip, which is likewise located in the measuring gap. The measuring chip has a heating means for this on a microstructured membrane, with which heating means part of the membrane is brought to a certain excess temperature, and a temperature-measuring unit, which is designed, for example, as a thermocouple (thermopile) and with which this temperature can be determined. In the presence of a paramagnetic gas, for example, oxygen, the specific heat conductivity of the oxygen component in the gas mixture changes due to cyclic modulation of the magnetic field, and this change will in turn lead to a variation of the measured temperature value, which can be determined, among other things, with a lock-in method. Since the magnitude of the temperature variations is also affected by the heat conduction properties of the other gases of the mixture, certain nonlinearities arise in the sensor characteristic, which depend on the nature of the gas components present.

SUMMARY OF THE INVENTION

The basic object of the present invention is therefore to make available a device for overcoming the above-mentioned drawbacks.

The object of the present invention is, in particular, to make available a measuring device
(a) to make it possible to selectively measure the oxygen concentration in a mixed gas against other admixtures,
(b) to make it possible to carry out a continuous determination of the oxygen concentration,
(c) to make available a sensor characteristic that is linear and independent from gas admixtures, and
(d) to make it possible to determine the concentrations of the added gases.

According to the invention, a device for measuring the concentrations of gases in a gas sample is provided comprising a modulatable magnetic flux source, which has an air gap, to which a gas sample can be fed. A controllable power source for generating current and voltage signals is coupled with the modulatable magnetic flux source to generate a modulatable magnetic flux within the air gap. At least two measuring points are arranged at least partly within the air gap wherein each measuring point has an electrically controllable temperature-dependent heating structure. Each measuring point is coupled with a variable power source to heat the corresponding heating structure to a working temperature. Each measuring point is coupled with a measuring circuit to measure heat conduction measured signals generated by the corresponding heating structure, from which the concentrations of gases, which are contained in the gas sample, can be derived.

Due to the nature of the above-described measurement, the various gases have different dependences on the working points (working temperature of the measuring chip, magnetic flux density, at which the $O_2$ measurement is carried out, ambient pressure) of the measuring device. The object is accomplished in that the measuring device known from DE 100 37 380 A1 is operated either with different operating parameters one after another or it is preferably equipped with at least one more heat conductivity measuring point, wherein this at least one additional heat conductivity measuring site is operated with different operating parameters. In other words, the at least two measuring points of the measuring device according to the present invention are operated in parallel with different operating parameters or with different working points. Both the thermal working points and the magnetic working points may be varied. It shall be noted that it is likewise possible to change the pressure working point.

Each measuring point has at least one heat conduction-measuring unit as well as one heating means, wherein any electric heating means may be used as the heating means. As an alternative, the heat conduction-measuring unit and the heating means may be designed as a combined heating and measuring element, and this combined element is preferably a heating wire or a similar hearting means, which can be heated to a desired temperature by supplying electric power and whose temperature values can be read. The heat conduction-measuring unit(s) and the one or more heating means and the combined heating and measuring element(s) is (are) arranged in the air gap of a magnetic circuit in said examples. These components are preferably integrated in one or more measuring chips, which are located in the air gap of the magnetic circuit. A measuring chip with a plurality of measuring points is preferably used. Such a measuring chip preferably has a microstructured membrane with a heating means formed thereon for each measuring point, with which a part of the membrane can be brought to a certain temperature by supplying electric power, and a heat conduction-measuring unit designed, for example, as a thermocouple (thermopile), with which this temperature can be measured.

As was explained above, the measuring means according to the present invention has at least one measuring point with a heating means each and at least one measuring unit, wherein the measuring points are preferably operated at different working points. To determine the gas concentration, the respective working temperatures of the heat-measuring units are determined simultaneously. As an alternative or in addition, the heat output (or the heating current or heating voltage) of the one or more heating means, which are necessary for this, the operating parameters characterizing the respective working point as well as optionally the changes in these parameters over time are determined.

For example, the following operating states or modes of operation are conceivable as possible operating states or modes of operation for operating the measuring device according to the present invention:
1. Operation of the measuring point(s) at different heat outputs or operating temperatures, statically and dynamically,
2. Operation of the measuring point(s) at different magnetic flux densities, wherein both static and dynamically variable magnetizations are conceivable, and
3. Operating pressure within the gas-measuring cell (likewise statically and dynamically). These operating states may be used both individually and combined and are defined such that the primary static and dynamic measured temperature signals of the measuring device can be used either as a measured value directly or as a controlled variable. The control signals needed for the control (for example, heat output, heating current, heating voltage or coil current for generating the magnetic field intensity) are then analyzed by measurement in the latter case.

The present invention will now be described on the basis of some exemplary embodiments with reference to the figures, which show various embodiments of the sensor according to the present invention and of the measuring device according to the present invention and explain the corresponding measurement methods. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
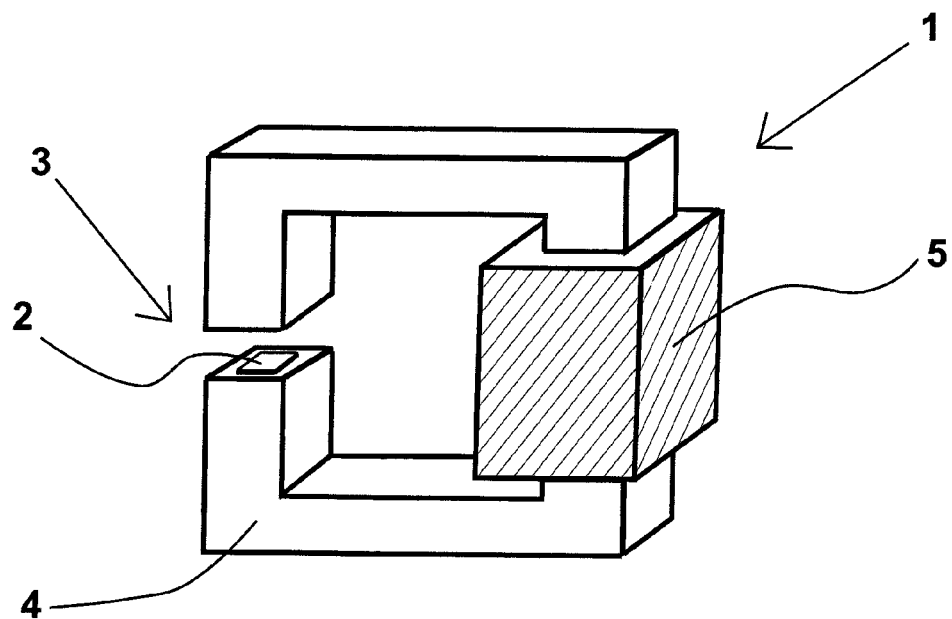
FIG. 1 is an exemplary embodiment of the measuring device according to the present invention in the form of an electromagnet, in the air gap of which a measuring chip is arranged.

Referring to the drawings in particular, FIG. 1 shows a preferred exemplary embodiment of the measuring device (or sensor) 1 according to the present invention for measuring the oxygen concentration or the concentration of another paramagnetic gas in a gas sample. The measuring device 1 has a measuring chip 2, which is arranged in the case being shown in the air gap 3 of an electromagnet 4 provided with a coil 5, so that an electrically controllable magnetic field can be applied to the measuring point of the measuring chip 2. However, a permanent magnet (not shown), by means of which a constant magnetic field is generated, may also be provided instead of coil 5. The measuring device 1 is designed, furthermore, to enable the gas to be analyzed (gas sample) to flow through the air gap 3 and past the measuring chip 2.

Figure 2:
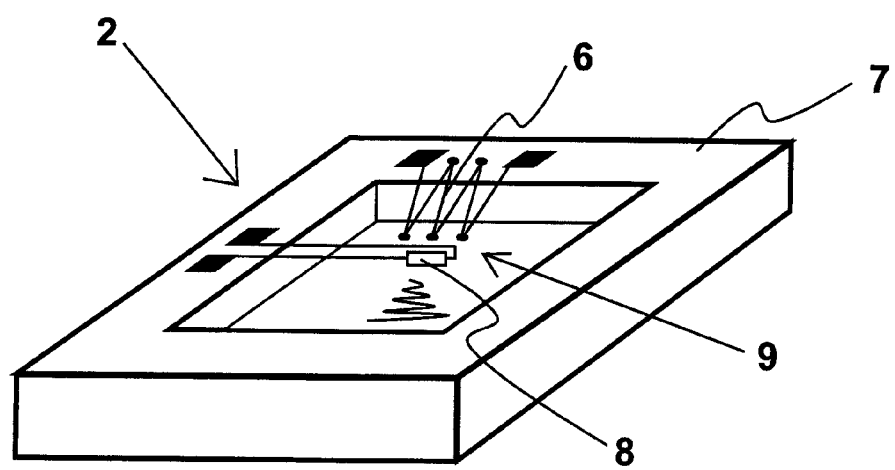
FIG. 2 is a detailed view of a measuring chip from FIG. 1 with a measuring point.

As is shown in detail in FIG. 2, the measuring chip 2 has, according to a first embodiment, a measuring point with at least one electrically controllable heat conduction-measuring unit 6, which is preferably designed as a thermocouple (thermopile). The measuring chip 2 may have a plurality of heat conduction-measuring units 6, which may be arranged at different sites. Furthermore, the measuring point may also be embodied by two or more separate individual chips or as a measuring chip with a plurality of measuring points, as this is described in detail in reference to FIG. 2a. The measuring chip 2 may have one or more perforated membrane(s) 7 for the entry of the gas of the gas sample from the top side. However, a closed membrane is preferably used, whose carrier frame is removed, e.g., according to the etching technique, to the extent that the gas to be measured can enter under the membrane through the gap formed. As an alternative, the volume having entered under the membrane may also be permanently filled with a poorly conducting gas (e.g., xenon).

The magnetic field generated by the coil 5 is preferably embodied as a pure alternating field with a time course symmetrical with the zero point. The time course is preferably sinusoidal, but it may also have other shapes (triangular or rectangular shapes). As an alternative or in addition, the magnetic field may be controlled in its amplitude. The amplitude control of the alternating magnetic field additionally leads, besides to the signal processing possibilities, to the advantage that the electric power for the measuring points can be reduced simultaneously with the magnetization at higher oxygen signal levels. However, magnetization controlled sequentially with a DC component is also conceivable, in which the modulated field component can be shifted on the magnetization characteristic. To keep the energy consumption for the magnetization low, it is also conceivable to generate the magnetic field at least partly with a permanent magnet.

As is also apparent from FIG. 2, measuring chip 2 has an electrically controllable heating means 8, which may be designed, for example, as an electrically conductive resistor structure deposited on the membrane or as a heating wire. The heating means is preferably arranged or designed to heat the membrane 7 of the measuring chip 2 to a desired temperature.

It shall be noted that the heat conduction-measuring unit 6 and the heating means 8 may be designed such that they are integrated as a temperature-dependent heating structure, i.e., a resistive heating/measuring element, in which the temperature measurement takes place with the use of the temperature coefficient. Examples of such heating structures are heating wires or similar heating means with a temperature-dependent resistivity. For the sake of clarity, these temperature-dependent heating structures are represented and described in the figures as separate heat conduction-measuring units 6 or heating means 8. Consequently, the measuring units 6 and the corresponding heating means 8 may be replaced, if technically meaningful, by integrated, temperature-dependent heating structures in the embodiments described.

The exemplary embodiments described below predominantly pertain, unless mentioned otherwise, to arrangements with two measuring points, which are arranged on a measuring chip 2. As an alternative, two measuring chips 2 operating in parallel with one measuring point each may be used as well. Each of the measuring points may be provided with one or more heat conduction-measuring units 6 in both cases.

Figure 2A:
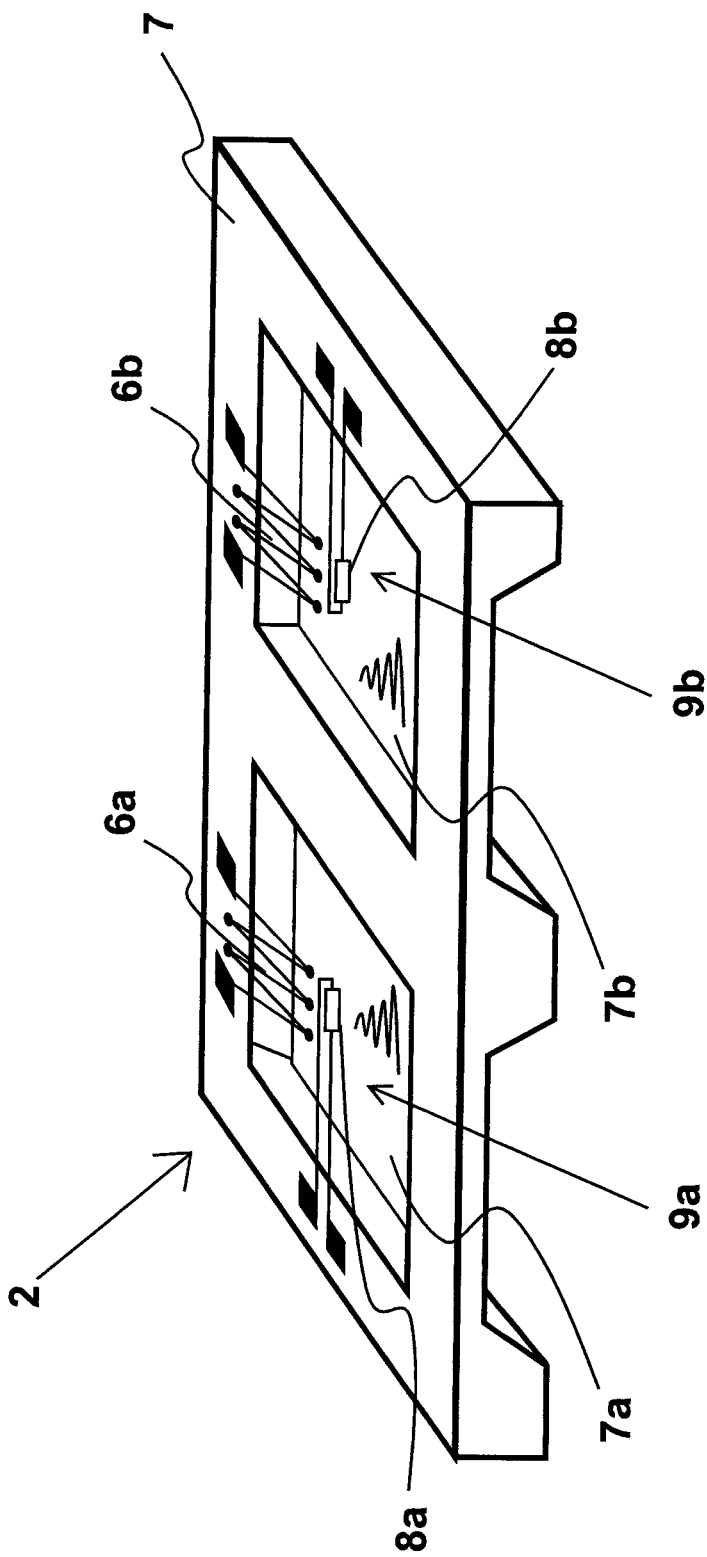
FIG. 2a is a detailed view of a measuring chip from FIG. 1 with two measuring points.

FIG. 2a shows an embodiment with a measuring chip 2, which has two measuring points 9a, 9b, which are arranged next to each other and which are provided each with a heat conduction-measuring unit 6a, 6b and a heating means 8a, 8b. As is also shown in FIG. 2a, the measuring units 6a, 6b and the heating means 8a, 8b are arranged on a cover layer 7 made, e.g., of Si3N4. This cover layer 7 may be exposed by etching from the underside at the sites at which the measuring units 6a, 6b and the heating means 8a, 8b are arranged. To make possible the entry of the measuring gas to be analyzed to both sides of the measuring points 9a, 9b, either the membrane 7a, 7b can be partly removed by etching, and the measuring chip 2 is etched partially to a small thickness, so that the entry of gas is possible from the front side. As was explained above, the measuring units and the corresponding heating means may each be replaced by integrated, temperature-dependent heating structures.

Figure 3:
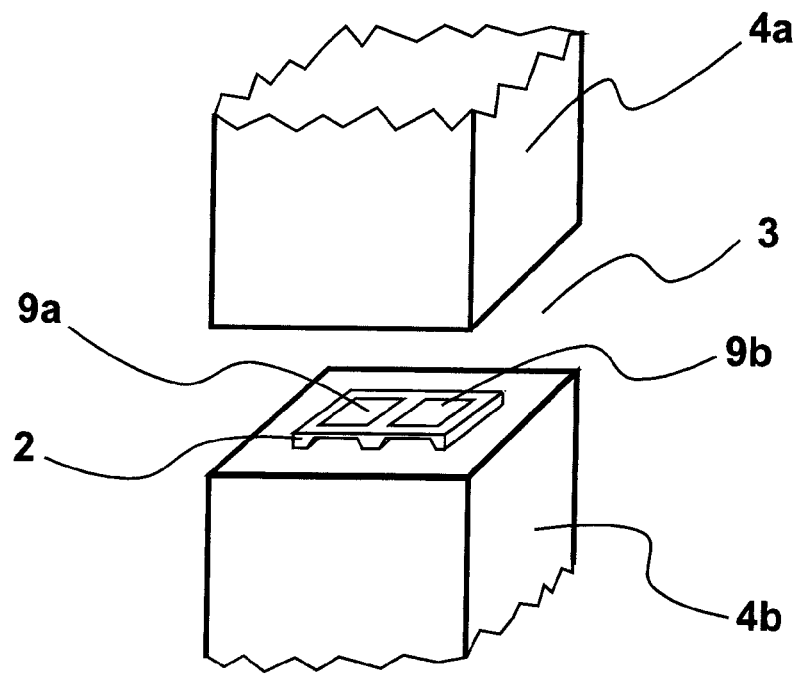
FIG. 3 is a detailed view showing the measuring chip with two measuring points from FIG. 2, which is arranged in the air gap of a magnet.

FIG. 3 shows a preferred embodiment, in which a chip 2 is used, which has two measuring points 9a, 9b with a heat conduction-measuring unit 6a, 6b each and a corresponding heating means 8a, 8b each. FIG. 3 shows the upper pole shoe 4a and the lower pole shoe 4b of the electromagnet from FIG. 1. The measuring chip 2 is arranged on the surface of the lower pole shoe in the air gap 3 between the two pole shoes, and measuring chip 2 has two measuring points 9a, 9b, which are arranged next to each other and contain a heat conduction-measuring unit 6a, 6b each and a corresponding heating means 8a, 8b each (not shown), as is shown in FIG. 2a. As was explained above, the two measuring points 9a, 9b may be integrated in one chip 2 (FIG. 2a). As an alternative, two or more chips with a measuring point each may be provided. It is, of course, also possible that the chip 2 shown in FIG. 2a has more than two measuring points.

The two measuring points 9a, 9b are preferably approached in parallel (i.e., simultaneously) with two different working points. However, the different working points may also be approached, in principle, sequentially, but, as was already mentioned, the gas mixture must be kept constant for the duration of the measurement.

If the two measuring points 9a, 9b are operated simultaneously at different working points (i.e., different heat outputs, different magnetic flux densities or different operating pressures), different voltages ($O_2$ signals), which correspond to the respective measured $O_2$ values, are also obtained from the two measuring units 6a, 6b. For example, periodic $O_2$ fluctuations can be separated from the respective base signals by simple filter means. The two resulting periodic $O_2$ signals and the non-periodic base signals are subsequently related to one another and analyzed in order to determine the current oxygen concentration at high accuracy. In addition, nonlinearities can be reduced by correlating the two periodic $O_2$ signals freed from the base signals with the nonperiodic base signals. The concentrations of added gases can also be determined in the same manner.

The heating means 8a, 8b of the two measuring points 9a, 9b are operated at different temperature working points in a first mode of operation, and there are a total of three fundamental types of actuation (the magnetizing means is partly omitted in the circuits to simplify the representation and only the actuation for one of the two measuring points is shown).

The operation at different heat outputs or operating temperatures (static and dynamic) will be described below.

Figure 4:
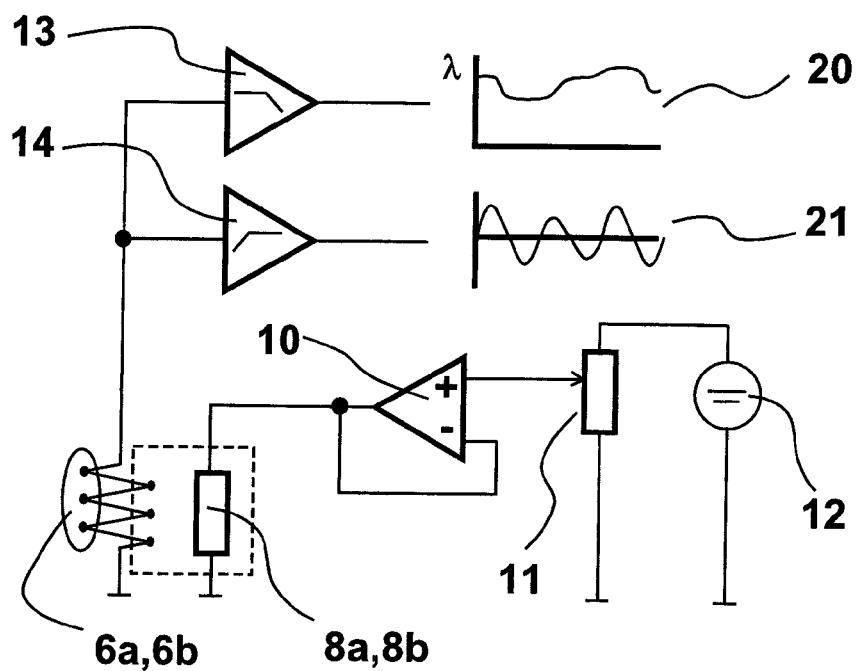
FIG. 4 is a schematic view showing a circuit for controlling one of the measuring points from FIGS. 2 and 2a with constant voltage.
Figure 5:
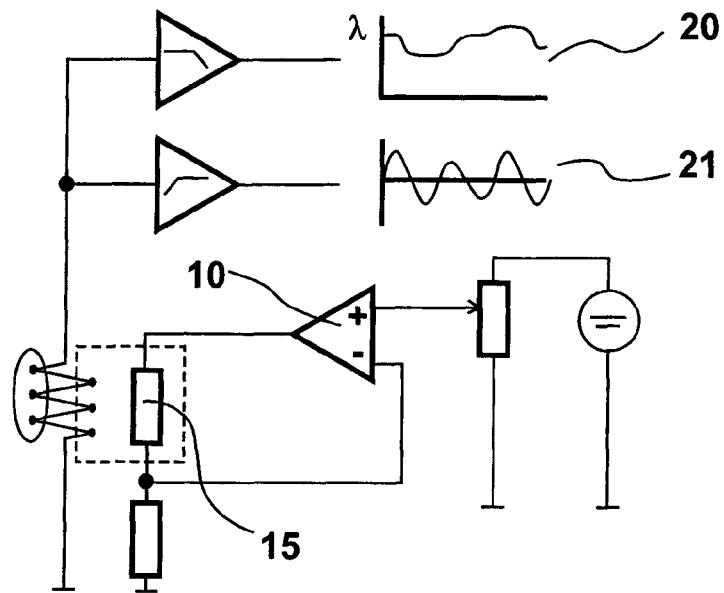
FIG. 5 is a schematic view showing a circuit for controlling one of the measuring points from FIGS. 2 and 2a with constant current.
Figure 6:
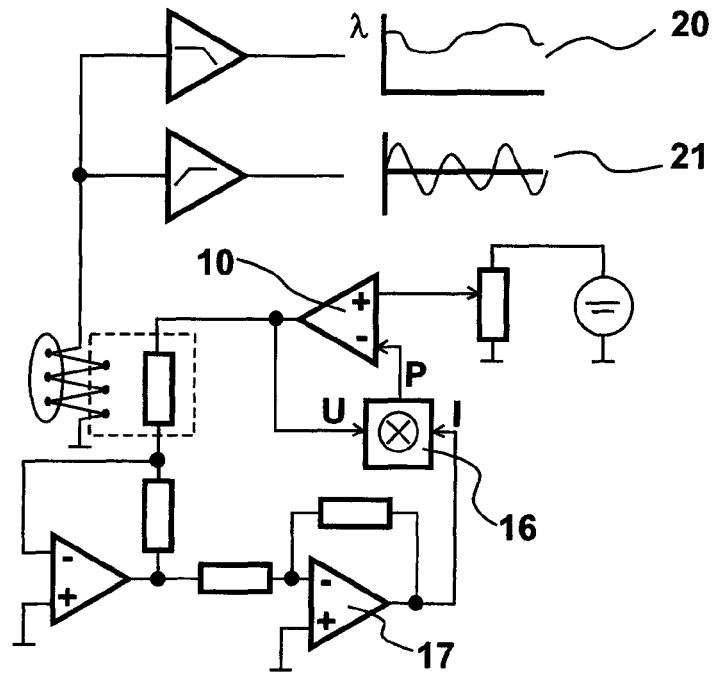
FIG. 6 is a schematic view showing a circuit for controlling one of the measuring points from FIGS. 2 and 2a with constant output.

In the first type of actuation, as is shown in FIGS. 4, 5 and 6, the two measuring points 9a, 9b, of which only one is shown, are operated with a constant heating voltage (FIG. 4), with a constant heating current (FIG. 5) or with a constant heat output (FIG. 6), which fit each the respective thermal working point of the heating means 8a, 8b, the necessary values being determined once in air and subsequently kept constant (calibration). The measured signals for the heat conduction 20 of the gas flowing past the measuring points 9a, 9b and the resulting periodic oxygen signals 21 can be found here in the voltages of the heat conduction-measuring units 6a, 6b.

The circuit design according to FIG. 4, based on control with constant voltage, will be described in more detail below. The heating means 8a, 8b is connected to a d.c. voltage source 12 via an amplifier 10 (connected as an impedance converter) and a voltage divider with variable tap. The output signal of the heat conduction-measuring unit 6a, 6b is sent via a low-pass filter 13 and a high-pass filter 14 in order to output the heat conduction signal 20 and the O₂ signal 21, respectively.

The circuit design according to FIG. 5, control with constant current, differs from the design from FIG. 4 only in that the amplifier 10 is connected as a non-inverting amplifier, wherein part of the output voltage of the amplifier is returned to the inverting input of the amplifier via a voltage divider comprising the heating means 8a, 8b and shunt 15.

The output (voltage) of the amplifier 10 connected to the first contact of the heating means 8a, 8b is coupled with the first input of a multiplier 16 in the circuit design according to FIG. 6, based on control with constant output, and the second input of the multiplier 16 (current) is connected to the second contact of the heating means via an inverting amplifier 17 as well as two multiplier resistors. The output of multiplier 16 is coupled with the inverting input of amplifier 10.

Figure 7:
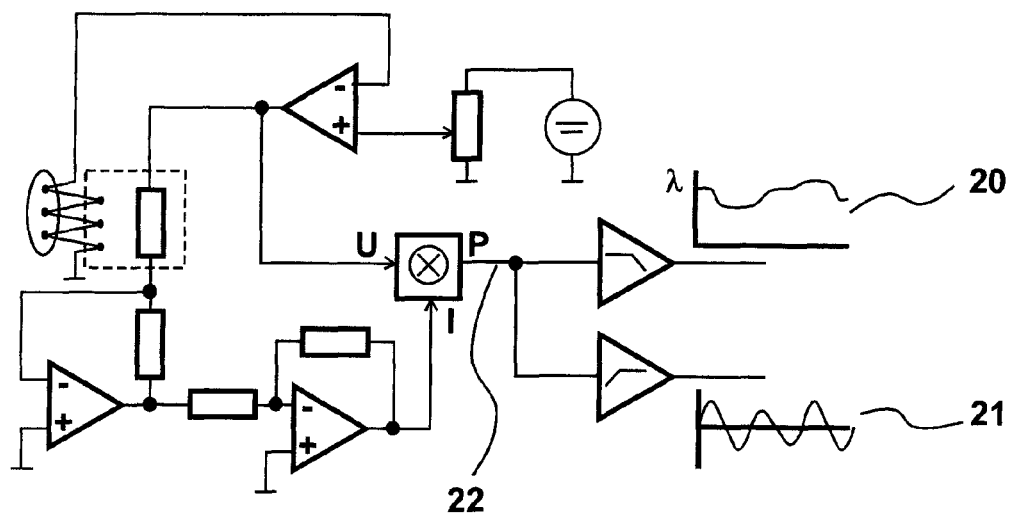
FIG. 7 is a schematic view showing a circuit for controlling one of the two measuring points from FIGS. 2 and 2a, in which the heat output is used as a measured signal.
Figure 8:
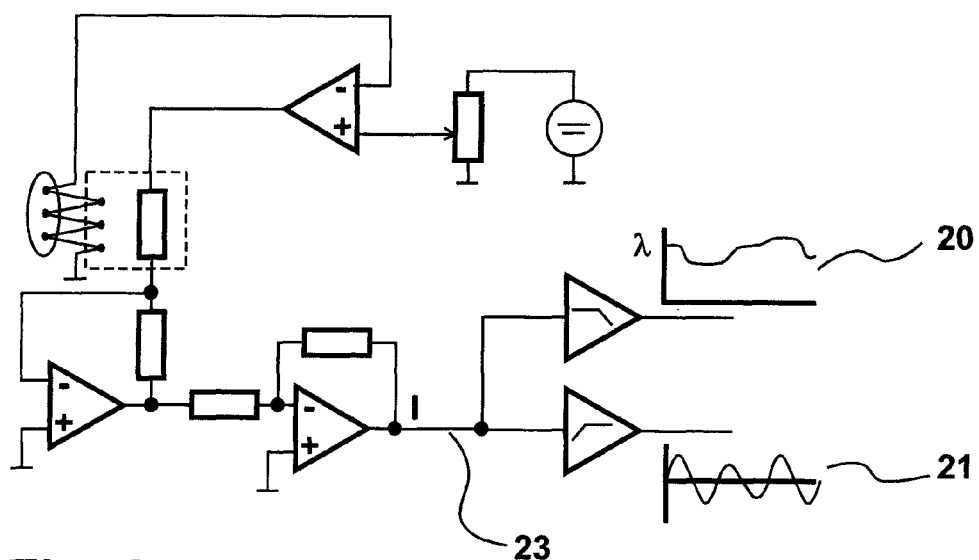
FIG. 8 is a schematic view showing a circuit for controlling one of the measuring points from FIGS. 2 and 2a, in which the heating current is used as a measured signal.
Figure 9:
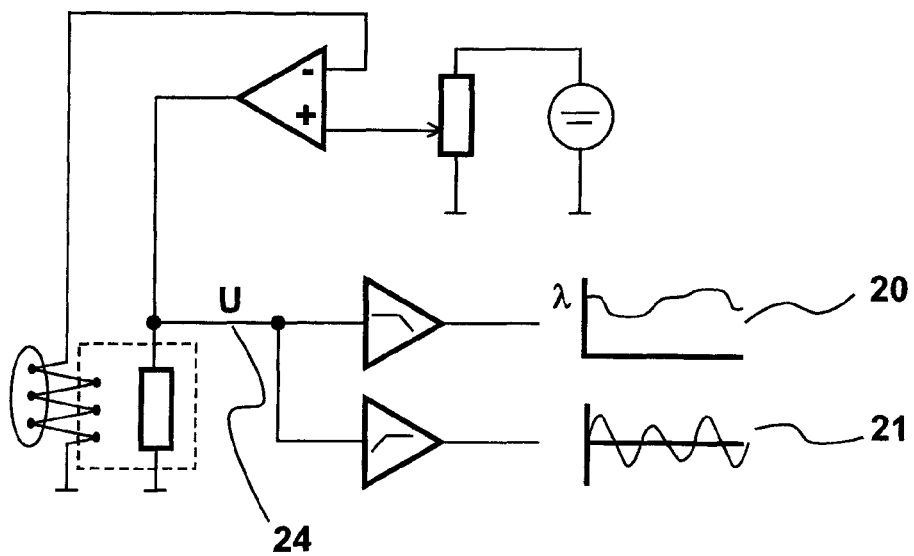
FIG. 9 is a schematic view showing a circuit for controlling one of the measuring points from FIGS. 2 and 2a, in which the heating voltage is used as a measured signal.

As is shown in FIGS. 7, 8 and 9, the respective thermal working points are adjusted to constant values independent from the gas composition in a second type of actuation. The output voltages of the heat conduction-measuring units 6a, 6b are used as controlled variables and the heating voltages, see FIG. 4, heating currents, see FIG. 5, and heat outputs, see FIG. 6, are adjusted. The necessary heating voltages 24, heating currents 23 and heat outputs 22 are the carriers of the measured signals in this case.

Figure 10:
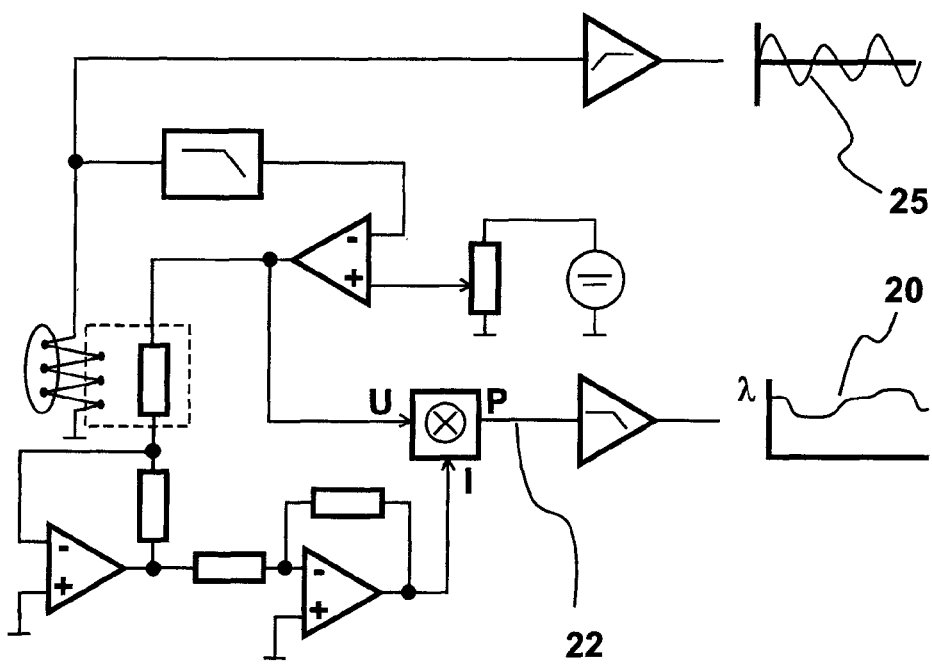
FIG. 10 is a schematic view showing a circuit for controlling one of the measuring points from FIGS. 2 and 2a, in which the heat output is used as a heat conduction signal and the thermoelectric voltage as an $O_2$ signal.
Figure 11:
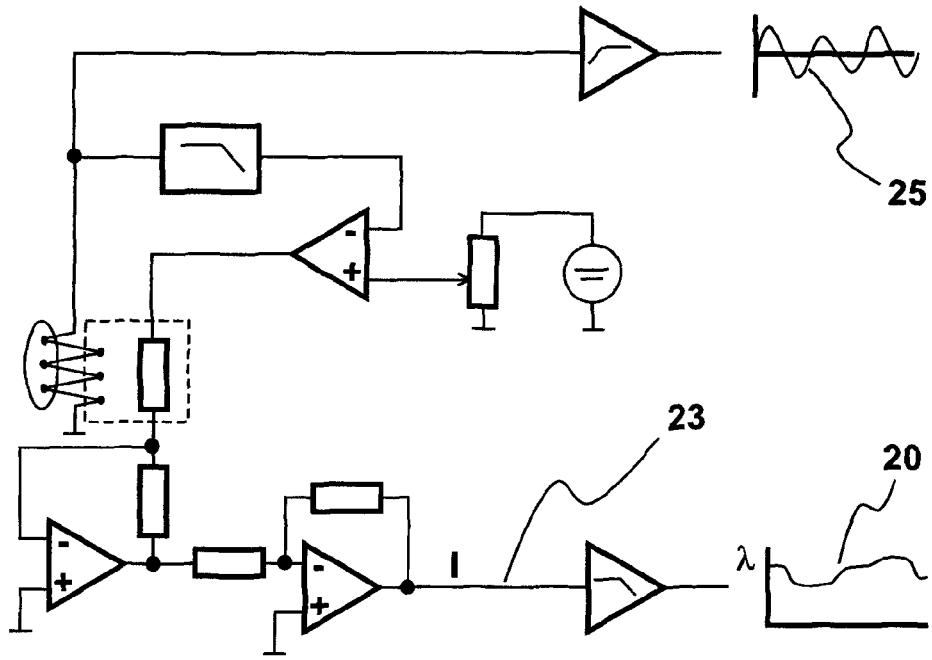
FIG. 11 is a schematic view showing a circuit for controlling one of the measuring points from FIGS. 2 and 2a, in which the heating current is used as a heat conduction signal and the thermoelectric voltage as an $O_2$ signal.
Figure 12:
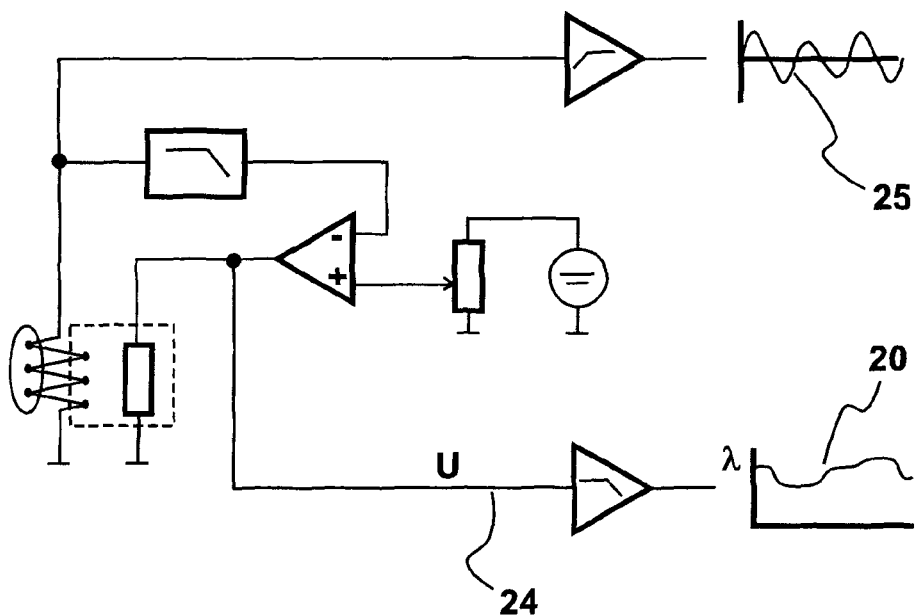
FIG. 12 is a schematic view showing a circuit for controlling one of the measuring points from FIGS. 2 and 2a, in which the heating voltage is used as a heat conduction signal and the thermoelectric voltage as an $O_2$ signal.

FIGS. 10, 11 and 12 show a third preferred type of actuation, which is a mixture of the above-mentioned two methods and combines the advantages of the operation at constant temperature level with the comparatively simple (because slow) temperature regulation. The output voltages of the heat conduction-measuring units 6a, 6b are used as controlled variables here and the heating voltages, heating currents and heat outputs are adjusted such that the working temperatures are constant in their average over time. The constant temperature mean values bring about stable measuring conditions, regardless of the nature of the gas mixture, while the rapidly changing oxygen signals 25 caused by the modulation remain directly measurable as temperature fluctuations, without bringing about any appreciable shifts of the working point because of their small amplitude. The control signals are conditioned with the use of electronic low-pass filters such that the temperature changes, which are caused by the gas mixture (and are slower) are deviation controlled, without the more rapid periodic heat conductivity changes caused by the magnetic field (measured oxygen signals) being interfered with.

Figure 14:
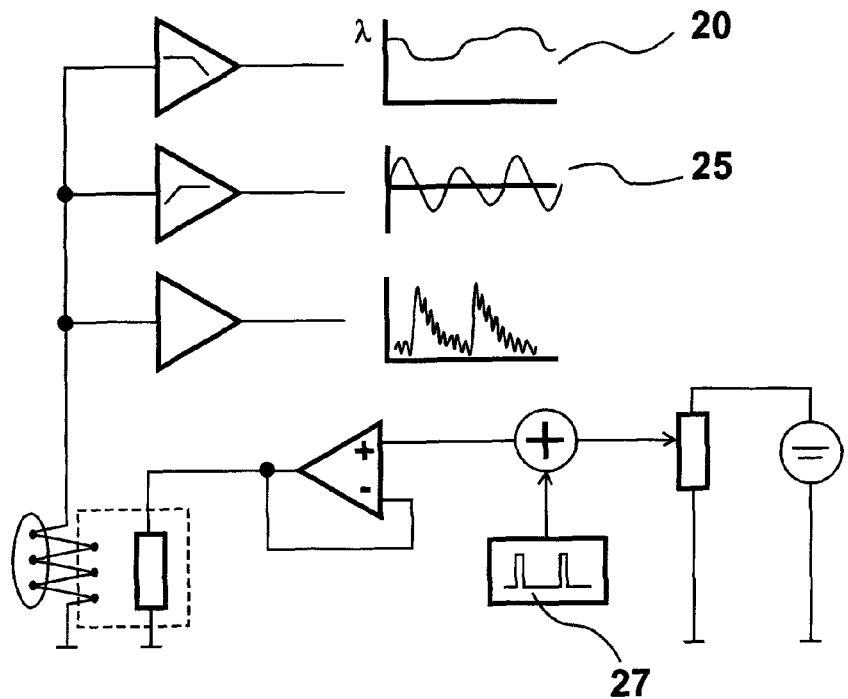
FIG. 14 is a schematic view showing a circuit for controlling one of the measuring points from FIGS. 2 and 2a, in which a pulsed signal is superimposed to the heating voltage.
Figure 15:
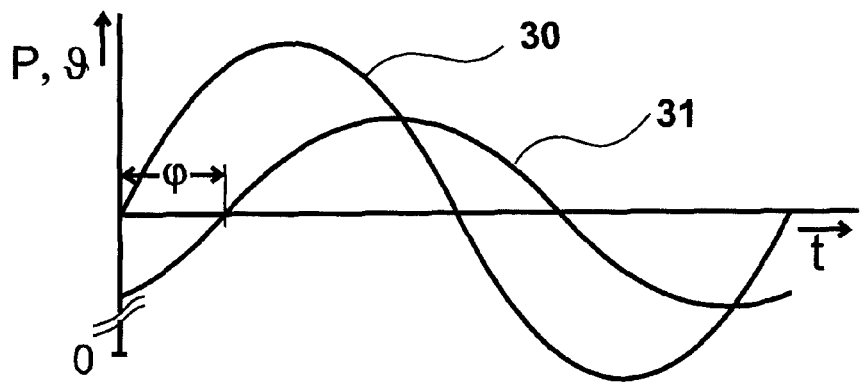
FIG. 15 is a diagram of the output signal of the circuit from FIG. 13.
Figure 16:
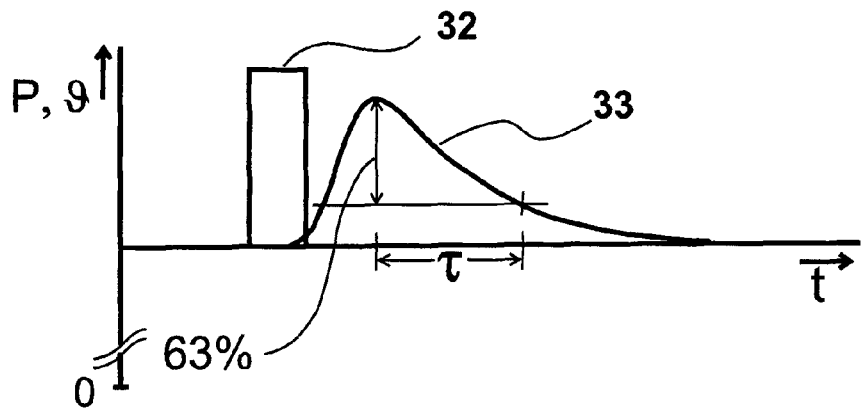
FIG. 16 is a diagram of the output signal of the circuit from FIG. 14.

In another type of actuation, the heating means 8a, 8b are additionally actuated at least partly with a heat output component that is variable over time. This component may be, for example, a sinusoidal heat output component 26 (FIG. 13) or a pulse-like heat output component 27 (FIG. 14). In case of an arrangement in which the heating element and the temperature-measuring element are identical (e.g., heating wire), information can be obtained on the dynamics of heat dissipation into the gas, which is determined essentially by the heat conduction and heat capacity values, by analyzing the relationship in time between the introduction of the heat output and the change in the temperature at the heating element. This effect occurs to an increased extent when using temperature pickups, which are separated in space, as they are logically used for microstructured heat conduction-measuring units 6a, 6b. When a sinusoidal temperature modulation is imposed on the heating element (FIG. 15), this can be measured as a phase shift and amplitude ratio between the heat output 30 and the measured temperature signal 31. If a pulsed change in the temperature of the heating means is used, curve 32, FIG. 6, the properties of the gas can be additionally inferred from the decay characteristic of the temperature pickup, curve 33. The damping of the temperature signals can also be used for an analysis.

Figure 13:
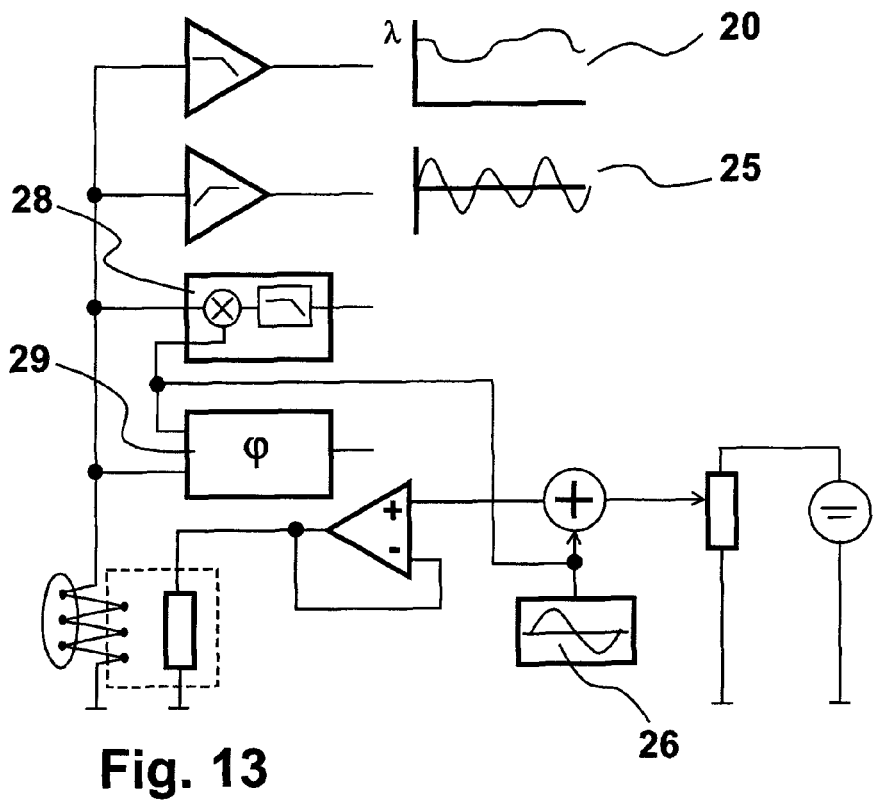
FIG. 13 is a schematic view showing a circuit for controlling one of the measuring points from FIGS. 2 and 2a, in which a sinusoidal signal is superimposed to the heating voltage.
Figure 17:
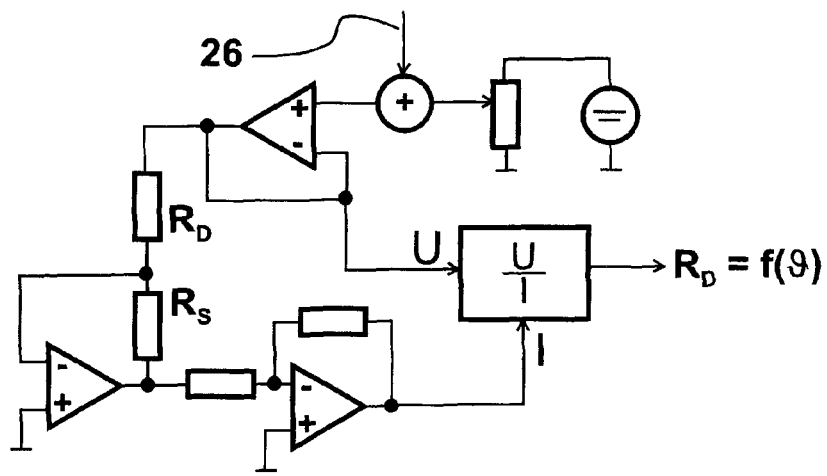
FIG. 17 is a schematic view showing a circuit for controlling a measuring point, in which a heating wire with temperature analysis is used as a combined heating and measuring element.

FIG. 13 shows, as an example, such an arrangement for the operation of a microstructured heating means with sinusoidal superimposition and actuation with constant heating voltage. The circuit additionally has a lock-in amplifier 28 and a phase detector 29. The sinusoidal additional signal is additively superimposed to the constant basic voltage and leads to a response at the thermocouple, which is offset in time, as a function of the nature and the concentration of the mixed gases. This mode of operation can be accordingly integrated in all the means shown in FIGS. 4 through 12. The change in the resistance of the heating means must be analyzed for the operation of a measuring unit with a heating wire to obtain a suitable temperature signal, and the wire temperature $R_D=f(\theta)$ can be inferred by using the temperature coefficient. This is schematically shown in FIG. 17.

FIG. 14 shows a circuit with pulsed superimposition. Since the spectral frequency components contained in the pulse response of the temperature signal cover a certain bandwidth and are superimposed with the signal components of the conventional heat conduction measurement and those of the O₂ measurement, complicated filtering of the raw signals is necessary, which is preferably carried out in a computer. Synchronization in time of the magnetization signals with the pulse signal simplifies here the signal processing, just as in the variant with superimposed sinusoidal signal 26 shown in FIG. 13.

The mode of operation at different magnetic flux densities will be explained below, with both static and dynamically changing magnetization being conceivable in this mode of operation.

Figure 18:
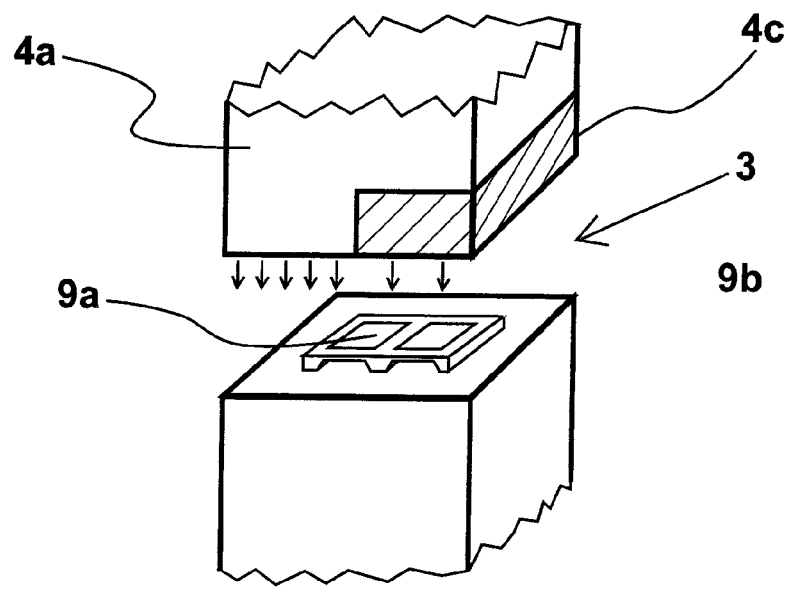
FIG. 18 is a detailed view of another exemplary embodiment of the measuring device according to the present invention in the form of a magnet, in the air gap of which the measuring chip from FIG. 2a is arranged and which has a stepped pole shoe.
Figure 19:
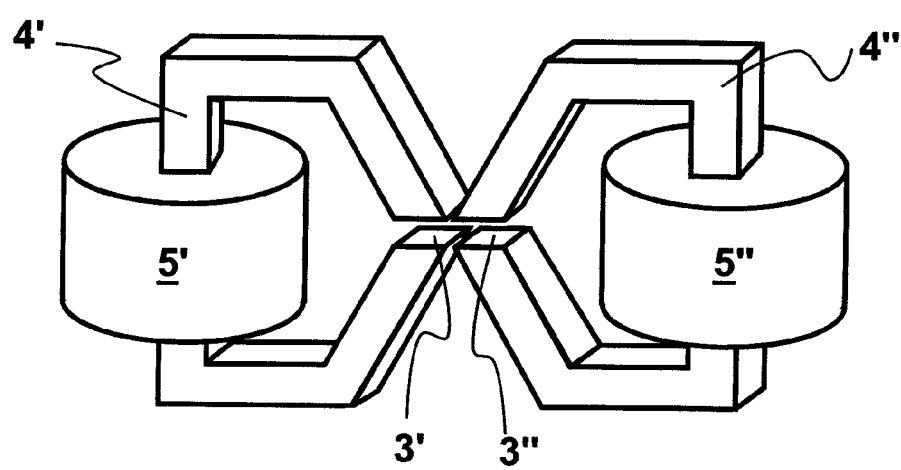
FIG. 19 is a view of an exemplary embodiment of the measuring device according to the present invention in the form of two separate magnetic circuits, in the air gap of which the measuring chip from FIG. 2a is arranged.

A first variant of this mode of operation operates with a modified magnet system (compare FIG. 3), in which the measuring points 9a, 9b located in the air gap 3 can be supplied with different magnetic flux densities. This can be achieved, for example, either by pole shoes having a stepped design in the air gap (FIG. 18) or by a second, independently controllable magnet system (FIG. 19). A section 4c made of a nonmagnetic material is used in the upper pole shoe 4a in the first case from FIG. 18, which leads to a fixed flux density ratio. As is apparent from FIG. 18, the left-hand part of the pole shoe 4a is located above the measuring point 9a, whereas the right-hand section 4c of the pole shoe, which section consists of nonmagnetic material, is arranged above the measuring point 9b. As a result, different flux densities are admitted to the measuring points 9a and 9b. It is obvious here that the magnetic flux can be generated by a coil (as in FIG. 1) or by a permanent magnet.

A variable flux density is obtained above both measuring points in the second case (FIG. 19) by providing two electromagnets 4' and 4", which can be magnetized variably by means of two separately controllable coils 5', 5". The measuring points 9a, 9b are arranged in the respective air gaps of the electromagnets 4' and 4". However, this variant requires increased technical effort. Instead of the two coils 5', 5", it is also possible to use two permanent magnets of different strengths, in which case a similar effect is achieved as in FIG. 18.

The amplitude-controlled magnetization operation shown in FIG. 19 can also be embodied with an individual, non-stepped magnet system (i.e., only one electromagnet instead of the two magnets 4' and 4" shown) and an individual measuring point. The amplitude control of magnetization can be used to regulate the magnetic field-modulated oxygen signal to a constant, preset value independently from the oxygen concentration. The concentration signal is then represented by the amplitude of the magnetizing current.

Figure 20:
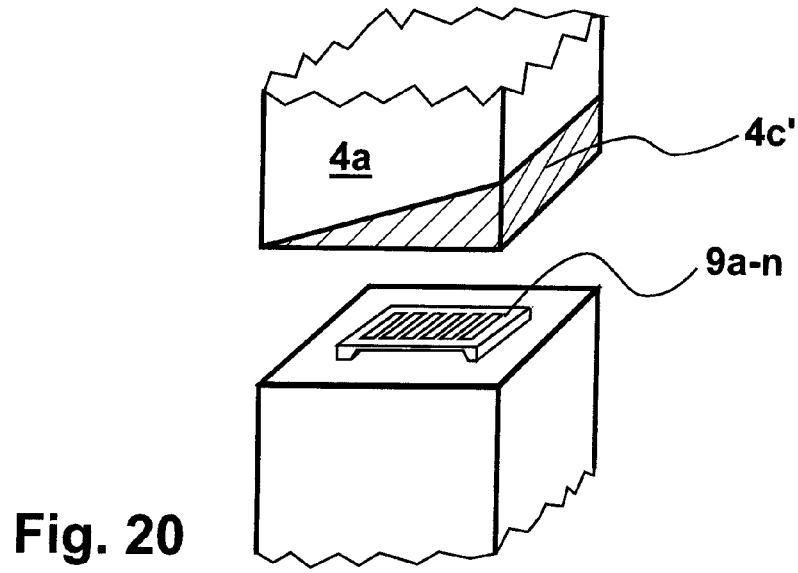
FIG. 20 is a detailed view of a variant of the exemplary embodiment from FIG. 18, in which a pole shoe is provided with a nonmagnetic wedge.

As was mentioned above, stable stepping of magnetization can be achieved in a fixed-stepped pole shoe (see FIG. 18) even with a permanent magnet. In addition, a wedge-shaped air gap may also be used in conjunction with a linear array of measuring points 9a-n or heat conduction-measuring means, as a result of which a plurality of measured values can be obtained at different flux densities. The wedge-shaped air gap can be embodied in a simple manner by beveling the lower surface of the pole shoe 4a facing the measuring points. As an alternative, a wedge-shaped element 4c' consisting of non-magnetic material may also be used instead of the cuboid element 4c consisting of nonmagnetic material (see FIG. 18), as this is shown in FIG. 20. It is obvious that the magnetic flux can be generated with a permanent magnet (constant magnetic field) or with a coil to generate an amplitude-modulatable magnetic field.

Figure 21:
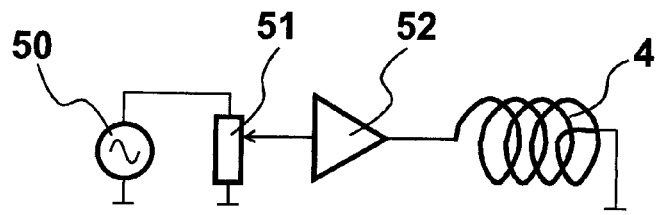
FIG. 21 is a schematic view showing a circuit for actuating a magnetizing coil for the measuring device according to FIGS. 1 and 3.
Figure 22:
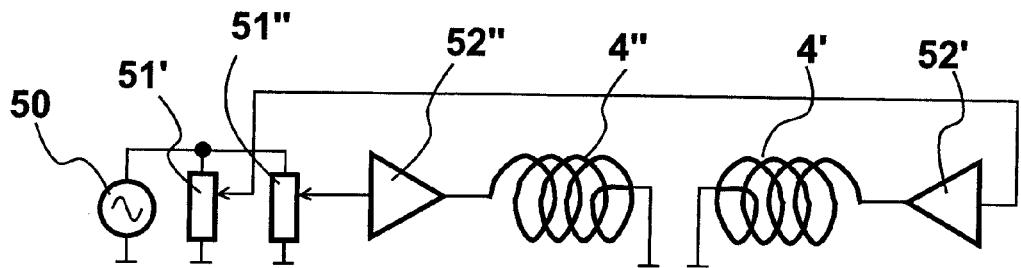
FIG. 22 is a schematic view showing a circuit for actuating two magnetizing coils for the measuring device from FIG. 19.

An electronic actuation is schematically shown in FIGS. 21 and 22. The arrays shown in FIGS. 4 through 14 may be used as analysis circuits. An amplitude-modulatable alternating voltage is applied in FIG. 21 to the magnetizing coil 4 by means of an alternating voltage source 50 via a voltage regulator 51 and an amplifier 52. An amplitude-modulatable alternating voltage each is applied in FIG. 22 to two magnetizing coils 4' and 4" (see FIG. 19) by means of an alternating voltage source 50 via two voltage regulators 51', 51" and corresponding amplifiers 52', 52".

On the whole, a plurality of measured variables can thus be obtained for the gas, which have different linear dependences and are difficult to calculate analytically. It is therefore proposed that multivariate regression methods be used for this. All the methods described can also be carried out with individual elements if the different working points are actuated one after another rather than simultaneously. However, it must be ensured in this case that the gas composition remains unchanged during the analysis.

While specific embodiments of the invention have been described in detail to illustrate the application of the principles of the invention, it will be understood that the invention may be embodied otherwise without departing from such principles.

Appendix

LIST OF REFERENCE NUMBERS

| | |
|---|---|
| 1 | Measuring device |
| 2 | Measuring chip |
| 3 | Air gap |
| 4 | Electromagnet |
| 5 | Coil |
| 6 | Heat conduction-measuring unit |
| 7 | Membrane(s) |
| 8 | Heating means |
| 9 | Measuring points |
| 10 | Amplifier |
| 11 | Voltage divider |
| 12 | D.c. voltage source |
| 13 | Low-pass filter |
| 14 | High-pass filter |
| 15 | Shunt |
| 16 | Multiplier |
| 17 | Inverting amplifier |
| 20 | Heat conduction signal |
| 21 | Oxygen signal |
| 22 | Heat output |
| 23 | Heating current |
| 24 | Heating voltage |
| 25 | Oxygen signal |

-continued

LIST OF REFERENCE NUMBERS

| | |
|---|---|
| 26 | Sinusoidal heat output component |
| 27 | Pulsed heat output component |
| 28 | Lock-in amplifier |
| 29 | Phase detector |
| 30 | Heat output |
| 31 | Measured temperature signal |
| 32 | Temperature of heating means |
| 33 | Decay characteristic at the temperature pickup |
| 50 | Alternating voltage source |
| 51 | Voltage regulator |
| 52 | Amplifier |

What is claimed is:

1. A device for measuring the concentrations of gasses in a gas sample, the device comprising:
at least one modulatable magnetic flux source providing an air gap or air gaps to which a gas sample can be fed;
at least one controllable power source for generating current and voltage signals, the at least one controllable power source being coupled with the at least one modulatable magnetic flux source to generate a modulatable magnetic flux within the air gap or air gaps;
at least two measuring points arranged at least partly within the air gap or air gaps, each of the measuring points having an electrically controllable, temperature-dependent heating structure;
a variable power source coupled with each of the measuring points to heat the corresponding heating structure to a working temperature; and
a measuring circuit coupled with each of the measuring points, each measuring circuit measuring heat conduction signals generated by the corresponding heating structure wherein the concentrations of gases, which are contained in the gas sample, is derived from the measured heat conduction signals, the measuring circuits being coordinately controlled for measurement in parallel using establishing a different set of operating parameters at each of the measuring points, wherein:
each temperature-dependent heating structure has an electrically controllable heating means and a heat conduction-measuring unit;
at least one of the measuring points is formed by a measuring chip with a membrane; and
the heating means is arranged or designed to heat the membrane to a desired temperature.

2. A device in accordance with claim 1, wherein the at least one modulatable magnetic flux source comprises an electromagnet coupled with a coil.

3. A device in accordance with claim 1, wherein the modulatable magnetic flux has a time course symmetrical with the zero point with one of a sinusoidal, triangular or rectangular shape, and wherein the amplitude of the magnetic flux can be additionally controlled.

4. A device in accordance with claim 1, wherein:
the at least one modulatable magnetic flux source has two pole shoes, between which the air gap is formed; and
the two measuring points are arranged at one of the pole shoes.

5. A device in accordance with claim 1, wherein the electrically controllable heating means comprises a resistance wire or heating wire.

6. A device in accordance with claim 1, wherein the at least two measuring points are arranged on a measuring chip.

7. A device in accordance with claim 1, wherein the two measuring points are operated simultaneously at different temperature working points.

8. A device in accordance with claim 7, wherein:
the two measuring points are operated during a measurement period with a constant heating voltage, with a constant heating current or with a constant heat output, which fit each of a respective thermal working point of the heating means.

9. A device in accordance with claim 7, wherein respective thermal working points of the measuring points are adjusted to constant values during a measurement period, wherein the output voltages of the heat conduction-measuring units are used as controlled variables and the heating voltages, heating currents or heat outputs are adjusted.

10. A device in accordance with claim 9, wherein necessary heating voltages, heating currents or heat outputs are the carriers of the measured signals.

11. A device in accordance with claim 7, wherein the heating means is additionally actuated during a measurement period with a heat output component that is variable over time, wherein the heat output component may be sinusoidal or pulsed.

12. A device in accordance with claim 7, wherein the magnetization signal is set such that at least one measured signal is adjusted to a constant preset value.

13. A device in accordance with claim 12, wherein the necessary magnetization amplitude is the carrier of the measured signal.

14. A device in accordance with claim 7, wherein:
an amplitude of the magnetic field generated by the modulatable magnetic field coil is adjusted to a constant preset value independently from the concentration of the gas to be measured.

15. A device in accordance with claim 1, wherein the at least two measuring points are operated sequentially at different temperature working points.

16. A device for measuring the concentrations of a paramagnetic gas in a gas sample, the device comprising:
one or more modulatable magnetic flux sources, each of the sources providing an air gap through which a gas sample can be fed;
one or more controllable power sources for generating current and voltage signals, the one or more controllable power sources being coupled with the one or more modulatable magnetic flux sources to generate a modulatable magnetic flux within the air gap or within the air gaps;
at least two measuring points arranged at least partly within the air gap or air gaps, each of the measuring points having an electrically controllable, temperature-dependent heating structure;
a variable power source coupled with each of the measuring points to heat the corresponding heating structure to a working temperature; and
a measuring circuit coupled with each of the measuring points, each measuring circuit measuring heat conduction signals generated by the corresponding heating structure wherein the concentrations of paramagnetic gases, which are contained in the gas sample, is derived from the measured heat conduction signals, wherein the at least two measuring points are arranged on a measuring chip.

17. A device for measuring the concentrations of gasses in a gas sample, the device comprising:
at least one modulatable magnetic flux source providing an air gap or air gaps to which a gas sample can be fed;
at least one controllable power source for generating current and voltage signals, the at least one controllable power source being coupled with the at least one modulatable magnetic flux source to generate a modulatable magnetic flux within the air gap or air gaps;
at least two measuring points arranged at least partly within the air gap or air gaps, each of the measuring points having an electrically controllable, temperature-dependent heating structure;
a variable power source coupled with each of the measuring points to heat the corresponding heating structure to a working temperature; and
a measuring circuit coupled with each of the measuring points, each measuring circuit measuring heat conduction signals generated by the corresponding heating structure wherein the concentrations of paramagnetic gases, which are contained in the gas sample, is derived from the measured heat conduction signals, wherein:
the at least one modulatable magnetic flux source has two pole shoes, between which the air gap is formed;
at least one of the pole shoes has a section formed of a nonmagnetic material, as a result of which regions with different magnetic fluxes are generated in the air gap; and
the at least two measuring points are arranged in regions of different magnetic fluxes.

18. A device in accordance with claim 17, wherein:
the different magnetic fluxes generated in the air gap include a reduced magnetic flux generated in some sections in the air gap; and
at least one of the measuring points is arranged in the region of the reduced magnetic flux.

19. A device in accordance with claim 17, wherein:
the section formed of a nonmagnetic material is an essentially wedge-shaped section formed of a nonmagnetic material.

* * * * *